(12) United States Patent
Strickler et al.

(10) Patent No.: US 6,479,715 B1
(45) Date of Patent: Nov. 12, 2002

(54) PROCESS FOR THE PREPARATION OF ALKYLENE GLYCOLS

(75) Inventors: Gary R. Strickler, Midland, MI (US); Guo-Shuh J. Lee, Midland, MI (US); William J. Rievert, Beaverton, MI (US); Daniel J. LaPrairie, Beaverton, MI (US); Edward E. Timm, Freeland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/042,699

(22) Filed: Apr. 9, 2002

Related U.S. Application Data

(63) Continuation of application No. 09/871,257, filed on May 31, 2001, now abandoned.

(51) Int. Cl.⁷ .............................................. C07C 27/00
(52) U.S. Cl. ..................................................... 568/867
(58) Field of Search ........................................ 568/867

(56) References Cited

U.S. PATENT DOCUMENTS

| | | | |
|---|---|---|---|
| 5,488,184 A | 1/1996 | Remen et al. | 568/867 |
| 6,137,015 A | 10/2000 | Strickler et al. | 568/867 |
| 6,160,187 A | 12/2000 | Strickler et al. | 568/867 |
| 6,211,419 B1 | 9/2001 | Strickler et al. | 568/867 |

FOREIGN PATENT DOCUMENTS

| | | |
|---|---|---|
| JP | 57-139026 | 8/1982 |
| RU | 2001901 | 10/1993 |
| RU | 2002726 | 11/1993 |
| WO | WO 95/20559 | 8/1995 |
| WO | WO 97/33850 | 9/1997 |
| WO | WO 99/12876 | 3/1999 |
| WO | WO 99/31033 | 6/1999 |
| WO | WO 99/31034 | 6/1999 |
| WO | WO 00/35842 | 6/2000 |

OTHER PUBLICATIONS

Kirk–Othmer, Encyclopedia of Chemical Technology, vol. 11, Third Edition, p. 929, 1980.

*Primary Examiner*—Alan Siegel
(74) *Attorney, Agent, or Firm*—Marie F. Zuckerman

(57) ABSTRACT

The present invention relates to a catalytic process for the preparation of alkylene glycols from alkylene oxide and water. Further, the invention relates to a method of preservation of catalysts in alkylene oxide containing systems. More in particular, it has been found that particular acids have a positive effect on the lifetime of catalyst systems based on anion exchange resins, and particularly those in the bicarbonate form.

13 Claims, No Drawings

PROCESS FOR THE PREPARATION OF ALKYLENE GLYCOLS

This application is a continuation of prior application U.S. Ser. No. 09/871,257 filed May 31, 2001 now abandoned.

FIELD OF THE INVENTION

The present invention relates to a catalytic process for preparing alkylene glycols from alkylene oxide and water. The preferred alkylene oxides include ethylene oxide, propylene oxide, and butylene oxide, and the preferred alkylene glycols include their respective monoalkylene glycols: ethylene glycol (EG), propylene glycol (PG), and butylene glycol (BG). Most preferably, the invention relates to the preparation of ethylene glycol from ethylene oxide and water. Particularly, the invention is directed to a method of preservation of catalysts in alkylene oxide containing systems.

BACKGROUND OF THE INVENTION

Alkylene glycols, such as ethylene glycol, propylene glycol and butylene glycol, are widely used as raw materials in the production of polyesters, polyethers, antifreeze, solution surfactants, and as solvents and base materials in the production of polyethylene terephthalates and polybutylene terephthalates (e.g. for fibers or bottles). Commercial processes for the preparation of alkylene glycols typically involve the liquid phase hydration of the corresponding epoxide in the presence of a large molar excess of water (see, e.g., Kirk-Othmer, Encyclopedia of Chemical Technology, Vol. 11, Third Edition, page 929 (1980)).

Ethylene glycol is commonly produced by the noncatalytic reaction of ethylene oxide and water. The reactions are run adiabatically, and the heat of reaction is absorbed by the reacting fluids which respond with an increase in temperature. The reaction temperature is typically 120° C. at the inlet to the reactor and often exceeds 180° C. at the exit point.

High temperatures are desirable in the preparation of ethylene glycol because the rate of reaction is maximized and selectivity is unaffected by high temperature. An added advantage of high temperature operation is that it reduces the need to supply external sources of heat to downstream purification equipment for the separation and recovery of unreacted water from the ethylene glycol product.

High ratios of water to ethylene oxide are typically fed to the commercial reactors to favor the production of mono-ethylene glycol, which is capable of also reacting with ethylene oxide to form diethylene glycol. Additionally, the diethylene glycol can react with ethylene oxide to form triethylene glycol, and so forth.

Formation of higher glycols is viewed as commercially unattractive, since the production of these higher glycols consumes valuable ethylene oxide, and markets for use of higher glycols are limited. The use of excessive quantities of water to favor mono-ethylene glycol, however, adds to the cost of manufacture because the excess water must be removed with energy through capital intensive evaporation and distillation process steps.

Catalytic systems have recently been studied for the purpose of selectively hydrolyzing epoxides, although commercialization has been an elusive goal.

For example, JP-A-57-139026 teaches a catalyzed process utilizing anion exchange resins in the chloride form in the presence of carbon dioxide resulting in superior selectivity over comparable non-catalyzed or thermal processes. One drawback to the process taught in said Japanese application is the formation of ethylene carbonate, separation of which is difficult and expensive.

Further developments at catalyzing the reaction of alkylene oxide and water, and particularly of ethylene and/or propylene oxide and water, have employed anion exchange resins in the bicarbonate form. For example, it has been shown previously that anion exchange resins in the bicarbonate form are particularly effective at catalyzing the hydrolysis of ethylene oxide. The selectivity of said reactions is high, often approaching 98% at water to ethylene oxide molar ratios less than 20:1.

More in detail, examples of such catalytic processes are taught in RU 2001901 and RU 2002726. The processes described therein require converting a catalyst to the bicarbonate form before the catalytic reaction, and reducing the concentration of carbon dioxide to as low as 0.01 wt. % in order to allow the catalyst to be more selective toward monoethylene glycol.

In addition, U.S. Pat. No. 5,488,184 also teaches a catalytic process wherein carbon dioxide is reduced or eliminated from the reaction mixture in order to enable higher reaction rates. This patent teaches that, for the bisulfite form of the catalyst, addition of carbon dioxide is beneficial to the reaction selectivity, but that for other anion forms of the catalyst, including the bicarbonate and formate forms, addition of carbon dioxide is detrimental to selectivity as well as the reaction kinetics for the bicarbonate form. The said patent thus teaches that the concentration of carbon dioxide be kept below 0.1 wt %. It also teaches using relatively low reaction temperatures of around 80° C. Such low reaction temperatures require external cooling.

International patent applications WO 99/31034 and WO 99/31033, corresponding to U.S. Pat. Nos. 6,160,187 and 6,137,015, respectively, also teach catalytic processes at relatively low reaction temperatures. Such references teach advantageously using a specific reactor design and adjusting the pH, respectively, to prolong the catalyst lifetime and minimize catalyst swelling. The aforementioned references are limited by low reaction temperature, due primarily to the fact that anion exchange resins in the bicarbonate form, if exposed to high temperatures, typically deactivate quickly, as quickly as a few days when temperatures exceed 120° C. Because the hydrolysis reaction is exothermic, even higher reaction temperatures would be desired to permit maximum temperature rise without cooling.

The catalysts used in the prior art documents discussed herein-above, and which are also useful in the process of the present invention, are based on a styrene-divinyl benzene polymer and are functionalized with a trimethyl amine attached to either a benzylic carbon which is attached to the polymer or through an alkyl or ether spacer which is attached to aromatic ring of the polymer resin. A selective form of the catalyst can be prepared by exchanging the anion with bicarbonate or metalate anions. These catalysts promote the reaction of EO with water, but to a much lesser extent promote the reaction of glycols with EO.

Unfortunately, these catalysts have been shown to swell unabatedly in the presence of the reactants while under reaction conditions by reacting with ethylene oxide. At reaction temperatures higher than 100° C., the catalysts swell at a rate of greater than 1% per day. In addition, these catalysts lose activity, and their half-life has been shown to be less than 1 year. Specifically, materials such as DOWEX MSA-1 (ex The Dow Chemical Company), Marathon A (ex The Dow Chemical Company), and XSA-1000 (ex Mitsubishi) swell due to their reaction with ethylene oxide and have half-lives of less than 100 days when a reaction temperature of higher than 100° C. is used.

In WO 99/12876 and WO 00/35 842, a process is described for the preparation of alkylene glycols by reacting an alkylene oxide with water in the presence of a catalytic composition based on a polybasic or a polycarboxylic acid derivative, which preferably is immobilized on a solid support. In WO 99/12876, the catalytic composition is based on ion-exchanging polymer materials containing as electropositive centers nitrogen atoms coordinated with anions of di- and/or tri- and/or polybasic acids in which one or more hydrogen atoms are substituted by an ion of an alkali metal and/or an ammonium ion.

WO 00/35842 appears to describe the same invention but describes the polycarboxylic acid derivatives as derivatives having in their chain molecule one or more carboxyl groups and one or more carboxylate groups, the individual carboxyl and/or carboxylate groups being separated from each other in the chain molecule by a separating group consisting of at least one atom. Suitable examples of such polycarboxylic acid derivatives are monosodium salts of citric acid and trimellitic acid. The solid support can be a solid material having electropositive sites as defined in WO 95/20559, or other ion exchange resins and especially anionic ion exchange resins.

The present inventors have studied this resin-based catalyst system of WO 00/35842 and conclude from the data in this international patent application, and especially in example 19 and further, that also this system has a problem with its citric acid catalyst losing activity.

To practice the above-described technology commercially with attractive economics will require that a catalyst be developed with good lifetime and swell properties. That is, commercialization of catalytic processes require that the catalyst be stable for an extended period of time. Otherwise, plant shut-downs to remove the catalyst from the reactor result in added expense and significant economic disadvantage.

A first method that at least partially solved this problem is described in U.S. Pat. No. B1-6,211,419 of the group of the present inventors. This patent relates to a method for making alkylene glycol, and preferably EG, PG or BG, comprising the steps of feeding an alkylene glycol and water to a reaction zone or, alternatively, to an adiabatic reactor, which reaction zone or adiabatic reactor comprises an anion exchange resin catalyst, which anion exchange resin preferably is in the bicarbonate form; co-feeding carbon dioxide to the reaction zone in an amount of at least 0.1 wt. %; and maintaining a temperature of at least 100° C. in the reaction zone. The advantages of this process are that swelling and loss of catalyst activity are considerably reduced.

The carbon dioxide co-fed in the reactor or reaction zone is, for the major part, also present in the end product, and should be removed. Unfortunately, this removal of carbon dioxide from the reaction products is expensive, requiring significant expenditures of capital and additional energy costs.

Thus an idealized catalytic system is one that provides a combination of long catalyst life with minimal physical or chemical complications while operating at high temperature with efficient use of energy.

SUMMARY OF THE INVENTION

In one aspect, the present invention is a method for making an alkylene glycol comprising: feeding an alkylene oxide and water to a reaction zone, the reaction zone comprising an anion exchange resin catalyst; feeding anion in acid form, selected from the group consisting of polycarboxylic acids containing at least two carboxylic acid groups to the reaction zone in an amount to reduce the swelling of said resin catalyst; while maintaining a temperature of at least 80° C. in the reaction zone.

In another aspect, the present invention is a method for stabilizing an anion exchange resin catalyst capable of catalyzing the reaction of alkylene oxide and water to alkylene glycol in a reaction zone, comprising co-feeding anion in acid form, selected from the group consisting of polycarboxylic acids containing at least two carboxylic acid groups to the reaction zone together with the alkylene oxide and water feed.

An important advantage of the present invention is that it allows anion exchange resins, and especially those in the bicarbonate form, to be used for the hydrolysis of alkylene oxides, and especially ethylene oxide, at temperatures exceeding 80° C. A further advantage of the present invention is that the rate of swelling is minimized and lifetime of the catalyst enhanced.

DETAILED DESCRIPTION OF THE INVENTION

In accordance with the present invention, it has been found that swelling and loss of activity in anionic exchange resins can be reduced by co-feeding certain carboxylic acids.

Without wishing to be bound to a particular theory, it is assumed that the resin based catalysts in anion form used in the processes of the prior art undergo thermal decomposition when they are placed in an aqueous medium that does not have any of the anion present and the temperature is above 80° C. To extend the useful life of the catalyst at temperatures above 80° C., it has according to the invention been found that anion should be added to the solution in its acid form. The amount of the anion required to provide stability depends on the temperature and the affinity of the anion for the resin.

While still not wishing to be bound to any theory, it is believed that the addition of the acid reduces the concentration of hydroxyl anion and thus decreases the amount of resin that exists in the hydroxyl anion form. It is believed in this regard that it is this hydroxyl anion form that lacks stability. Since equilibrium exists between all anions in the solution, the rate of decomposition appears to be proportional to some order of the concentration of hydroxyl anion in solution.

This invention is in one aspect a method for making glycols from alkylene oxides, or epoxides, and water. The preferred epoxides include ethylene oxide (EO), propylene oxide (PO), and butylene oxide (BO), and the preferred alkylene glycols include their respective monoalkylene glycols: ethylene glycol (EG), propylene glycol (PG), and butylene glycol (BG). Most preferably, monoethylene glycol is prepared from ethylene oxide and water.

The first step of the method of the present invention in this aspect comprises feeding water and an epoxide to a reaction zone. The reaction zone preferably comprises at least one adiabatic reactor containing a catalyst bed. The term "adiabatic reactor" is defined as a reactor having substantially no heat removed therefrom. In an adiabatic reactor, the temperature rise can be controlled by feeding a large excess of water to allow the heat to be absorbed by the water feed. The adiabatic reactor is usually a cylindrical vessel or series of vessels with no heat transfer between vessels, operated in plug flow manner to obtain maximum monoglycol selectivity.

The reaction zone is desirably maintained under conditions such that the epoxide and the water react to form a glycol product stream comprising glycol and water. For purposes of this invention, the "glycol product stream" shall be read broadly to include any product stream exiting a reactor which contains at least glycol and water. The glycol product is generally in mixture, solution, or contained within unreacted water.

In light of the disclosure herein, conditions which are conducive for the reaction to occur are within the skill in the art. Factors for consideration include the optimum temperature, pressure, and water to alkylene oxide ratio for reacting the feed stream(s) without providing conditions which significantly degrade the catalyst bed or selectivity to the desired product.

One of the conditions conducive to reacting the epoxide and water to form a glycol product stream is the temperature in the reactor. High temperatures are desirable in the preparation of glycol because the rate of reaction is maximized, and the amount of unreacted epoxide is reduced. The reaction temperature in a catalytic reactor should be at least 80° C. Preferably, a temperature of at least 100° C., and more preferably of at least 110° C. is maintained; even more preferably, a temperature of at least 115° C. is maintained, and most preferably, a temperature of at least 120° C. is maintained in the catalytic adiabatic reactor. Preferably, the temperature in the catalytic reactor is not more than 150° C., more preferably not more than 145° C., even more preferably not more than 140° C., and still even more preferably not more than 135° C.

The reaction pressures are generally in the range of about 100 kPa to about 10000 kPa, preferably 500 kPa to about 5000 kPa, with the intent to maintain reactants in the liquid phase.

In the reaction zone, a catalyst bed must be included, preferably in at least one adiabatic reactor in the reaction zone. Typically the catalyst bed is a fixed catalyst bed, but it may be a fluidized bed, a moving bed, or a slurry. It is desirable to minimize the volume of liquid in the catalyst bed to reduce the required reactor volume and to minimize noncatalytic reactions which may lead to lower monoglycol selectivity. Thus, a fixed bed is preferred over other types of catalyst beds.

The catalyst bed may comprise any material capable of catalyzing the desired reaction in the reaction zone, and in particular in the adiabatic reactor, in which it is employed. It should be of such a nature as to allow reactants and products to pass through the bed, yet provide a sufficient surface area for catalytic contact. Desirably, the catalytic material is solid and is insoluble in either the reactants or the glycol products under the conditions in the process.

Preferably, the catalyst for this invention is an anion exchange resin. In light of the disclosure herein, selection of a suitable anion exchange resin is within the skill in the art. Preferably, such anion exchange resin is a strong base anionic exchange resin converted to the bicarbonate form, to the citrate form or to the oxalate form. Illustrative of bicarbonate form exchange resins are the disclosures of WO 95/20559, WO 97/33850, WO 99/12876, WO 00/35842, RU Patent Nos. 2002726 and 2001901 (each of which is incorporated herein by reference). It is particularly preferred that the anion exchange resins contain quaternary ammonium groups. Examples of suitable, commercially available, anion exchange resins include: Amberlite™ IRA 400 and 900 series (based on polystyrene resins, cross-linked with divinylbenzene) (Rohm and Haas); Lewatit™ 500 WS (Bayer); Duolite™ A 368, A-biD, ES-131 and A-161 (Rohm and Haas); DOWEX™ MSA-1, MARATHON A, and MARATHON MSA; and DIAION™ XSA 1000 (Mitsubishi). Anion exchange resins with trimethyl benzyl ammonium groups (i.e., Type I resins) are particularly preferred for this invention.

In the most preferred embodiment the anion exchange resin has a counter anion in the bicarbonate form. However other suitable forms include citrate or oxalate.

The second step of the method includes feeding anion in acid form, selected from the group consisting of polycarboxylic acids containing at least two carboxylic acid groups, to the reaction zone. The co-fed anion is preferably fed in amounts which are just sufficient to reduce the swelling of said resin catalyst and provide a desired economic lifetime and stability to the catalyst. The appropriate amounts will depend on the temperatures used in the reactor, as will be evident from the discussion which follows.

The present inventors have found that at 120° C., for example, 1000 ppm of $CO_2$ (in accordance with the invention described in U.S. Pat. No. B1-6,211,419), 25 ppm of citric acid or 25 ppm of oxalic acid offer good protection against swelling. The use of 25–100 ppm of tricarballylic acid and 25 ppm of EDTA in the feed stream led to positive effects on the swelling behavior, as well, although these advantages were less than obtained for citric acid and oxalic acid. However, using 140 ppm of $CO_2$, 100 ppm of salicylic acid, 25 ppm of ascorbic acid, or 25 ppm of lactic acid in the feed stream did not lead in the inventors' opinion to sufficient beneficial effects on swelling when reaction temperatures exceed 120° C. Moreover, the latter mentioned group with the exception of $CO_2$ showed that mono-ethylene glycol selectivity is harmed during the course of the reaction; also when using tricarballylic acid and EDTA such a shift in selectivity was found.

The addition of polycarboxylic acid containing at least two carboxylic acid groups, and especially citric acid and oxalic acid, offer cost and capital advantages over the $CO_2$ process described in U.S. Pat. No. B1-6,211,419.

As stated herein-above, the amount of the anion required to provide stability and/or to reduce swelling of the resin catalysts depends on the temperature and the affinity of the anion for the resin. Preferably, the anion in acid form is selected from the group consisting of citric acid and oxalic acid; most preferably, the anion in acid form is citric acid.

Generally, the anion in acid form is fed to the reaction zone in a concentration of between 10 and 150 ppm, drawn to the total feed. Below 10 ppm, benefits are marginal and above 150 ppm advantages are offset by additional costs.

The preferred carboxylic acid concentration range is related to temperature. At higher reaction temperature, it is preferred to use a higher carboxylic acid concentration to achieve the best lifetime with least swelling. And at lower reaction temperature, the process can be operated at lower carboxylic acid concentration to achieve the best productivity and selectivity. On the basis of this information, a person of ordinary skill in the art can dependent on his process and equipment determine suitable amounts of carboxylic acid without undue burden.

Generally, the preferred range for carboxylic acid addition, and specifically citric acid addition, is between 25 and 100 ppm. Citric acid has been shown to reduce catalyst swelling when fed in a concentration of 25 to 100 ppm. In the examples (vide infra), it is demonstrated that the addition of small amounts of citrate anion results in a swelling rate that is less than those measured in experiments where no additive is added. Moreover, catalyst activity as measured by conversion is preserved when compared to systems where no additive is added.

Therefore, the present invention is also directed to a method for stabilizing an anion exchange resin catalyst capable of catalyzing the reaction of alkylene oxide and water to alkylene glycol in a reaction zone, comprising co-feeding anion in acid form, selected from the group consisting of polycarboxylic acids containing at least two carboxylic acid groups to the reaction zone together with the alkylene oxide and water feed. Examples of suitable carboxylic acids include, but are not limited to oxalic, citric, tricarballylic and ethylene diamine tetra acetic acid.

In this stabilization method, the anion in acid form is preferably selected from the group consisting of citric acid and oxalic acid; and most preferably is citric acid. A stabilizing amount is an amount of anion in acid form leading to a swelling rate being at least 1 volume % per day, and preferably at least 1.5 volume % per day lower than when no anion in acid form is co-fed in the reaction zone. The stabilizing amount for the anion in acid form that is fed in the reaction zone is generally in the range of 10–150 ppm.

The method of the present invention enables the catalyst to be removed or replaced less frequently than would otherwise be necessary. Catalyst degradation can be represented by catalyst half-life, which is defined as being the amount of time required for the catalyst to lose half of its catalytic activity. Preferably, a sufficient amount of acid anion is added so that the half-life of the catalyst used in the present invention is increased by at least 20 days relative to operation without acid anion, more preferably the half-life is increased by at least 40 days, and even more preferably the half-life is increased by at least 60 days. Preferably, at an operating temperature of 120° C., the catalyst half-life is at least 40 days.

The method of the present invention also reduces the amount of swelling that the catalyst undergoes. Preferably, using the method of the present invention, the rate of continuous, unlimited swelling is reduced by at least 50% relative to operation without the addition of acid anion, more preferably at least about 60%, and even more preferably at least about 70%.

Of course, the catalyst half-life and the rate of catalyst swelling will depend upon the specific catalyst. More swelling can be tolerated with a catalyst having a higher activity.

For the practice of this invention, waters of different purity may be used such as fresh water, deionized water, steam distilled water, condensate water (which may contain some residual glycol compounds), and also recycled water recovered from the dehydration process in the production of alkylene oxide and alkylene glycol (which may contain residual glycol). The water is provided in an amount which is in a stoichiometric excess of that required for forming a desired glycol from reaction with epoxide. Preferably, the molar feed ratio of water to epoxide is at least about 1.1, more preferably at least about 2.0, and even more preferably at least about 5.0. Preferably, the molar feed ratio is no more than about 50, more preferably no more than about 30, and even more preferably no more than about 20. Those of skill in the art will recognize that this ratio will vary depending upon the epoxides employed, the reaction conditions, and the specific catalyst utilized.

The epoxide used in the present invention can be unfinished epoxide containing small levels of impurities such as, for example, aidehydes, or the epoxide can be pure epoxide. The water and epoxide feed may be fed to the reaction zone separately or together as co-feed. The water and epoxide may be fed to the reactors as a gas, as a liquid, or as a combination thereof.

The invention will now be described in more detail, while referring to the following comparative examples and examples according to the invention. Any reference to percentages is a reference to weight percentages drawn to the total weight of the composition or reactor contents, unless otherwise indicated.

EXAMPLES

Example 1 (Comparative)

For example 1, 15 ml of Mitsubishi Diaion XSA-1000 anion exchange resin was placed in a beaker that contained 50 ml of water. $CO_2$ gas was bubbled through the flask for 16 hours to convert the XSA-1000 anionic exchange resin from the hydroxyl form to the bicarbonate form.

The exchanged catalyst was placed in a tubular reactor, equipped with a hot oil jacket to permit nearly isothermal operation. More in detail, the reactor was a jacketed, 1.1 cm inner diameter, 23 cm long, 316 Stainless Steel tube.

The reactor shell was heated to 120° C. by circulating hot oil through the jacket. Water at a rate of 1.07 ml/min was mixed with ethylene oxide at a rate of 0.16 ml/min and fed continuously to the reactor. The temperature in the reactor was monitored by a multipoint thermocouple, and it was found that the reactants increased in temperature due to the exothermic reaction as they passed through the bed of catalyst. The maximum temperature in the bed was about 10° C. hotter than the oil bath set point, reaching a maximum of 130° C. The effluent leaving the reactor was analyzed by an on-line gas chromatograph.

Initially, the conversion was 99% and the selectivity to the monoglycol was 98.1%. The reaction was continued for 15 days at which point the reactor shut down due to excessive pressure drop. The catalyst had swelled to twice its original volume and plugged the reactor. At the end of the run, the conversion and selectivity were 96.0% and 98%, respectively. The resin swelling rate was 6.7%/day.

Example 2 (Comparative)

For Example 2, a catalyst was prepared using Dow's Marathon A Anion Exchange Resin. The resin was converted from the chloride to the anion form by placing a catalyst sample in a tube and slowly pumping 1 gallon of an aqueous solution of sodium bicarbonate (5 wt. %) though the tube for a period of 16 hours.

The exchanged catalyst was placed in a tubular reactor and operated as described in Example 1. The maximum temperature in the bed was about 10° C. hotter than the oil bath set point, reaching a maximum of 118° C.

The reaction was continued for 27 days at which point the reactor was shut down. At the end of the run, the conversion and selectivity (to MEG) were 99.8% and 97.6%, respectively. The resin swelling rate was 2.1%/day.

Example 3 (Comparative)

For Example 3, the procedure used in Example 2 to prepare the catalyst and to start the reaction was repeated. In this example, the maximum reaction temperature was allowed to reach 125° C.

At the beginning of the run, the conversion and selectivity were in excess of 99.9% and 98.7%, respectively. The reaction was continued for 21 days at which point the reactor shut down due to excessive pressure drop. The catalyst had swelled to twice its original volume and plugged the reactor. At the end of the run, the conversion and selectivity were 99.7% and 98.1%, respectively. The resin swelling rate was 5.1%/day.

Example 4 (Comparative)

For Example 4, the procedure used in Example 2 to prepare the catalyst and to start the reaction was repeated. In this example, the maximum reaction temperature was allowed to reach 130° C.

At the beginning of the run, the conversion and selectivity were more than 99.9% and 98.7%, respectively. The reaction was continued until the reactor shut down due to excessive pressure drop, as the catalyst had swelled to twice its original volume and plugged the reactor. At the end of the run, the conversion and selectivity were 99.7% and 98.1%, respectively. The resin swelling rate was 10.1%/day.

Example 5 (Comparative)

For Example 5, the procedure used in Example 2 to prepare the catalyst and to start the reaction was repeated. In this example, the maximum reaction temperature was allowed to reach 133° C.

The reaction was continued for 6 days at which point the reactor shut down due to excessive pressure drop. At the end of the run, the conversion and selectivity were 100% and 97.4%, respectively. The resin swelling rate was 17.4%/day.

Example 6

For example 6, the procedure used in Example 2 to prepare the catalyst and start the reaction was repeated. In this example, the maximum reaction temperature was allowed to reach 130° C. To demonstrate the benefits of adding an anion feed additive on the rate of swelling, 25 ppm by weight of citric acid was added to the aqueous feed. Initially, the conversion was more than 99.9% and the selectivity was 97%.

The reaction was continued for 29 days at which point the reactor shut down due to excessive pressure drop. The catalyst had swelled to more than twice its original volume and plugged the reactor. At the end of the run, the conversion and selectivity were in excess of 99.9% and 96.9%, respectively. Even though the temperature was 130° C., the resin swelling rate was only 3.9%/day.

Example 7

For example 7, the procedure used in Example 2 to prepare the catalyst and to start the reaction was repeated. In this example, the maximum reaction temperature was allowed to reach 130° C. To demonstrate the benefits of adding an anion feed additive on the rate of swelling, 50 ppm by weight of citric acid was added to the aqueous feed. Initially, the conversion was more than 99.0% and the selectivity was 97.8%.

The reaction was continued for I 5 days. At the end of the run, the conversion and selectivity were more than 98.6% and 98.1%, respectively. Even though the temperature was 130° C., the resin swelling rate was further reduced to 1.3%/day.

Example 8

For example 8, the procedure used in Example 1 to prepare the catalyst and to start the reaction was repeated. In this example the maximum reaction temperature was allowed to reach 130° C. Initially, the conversion was greater than 99.9% and the selectivity was 98.1%. To demonstrate the benefits of adding an anion feed additive on the rate of swelling, 25 ppm by weight of citric acid was added to the aqueous feed.

The reaction was continued for 34 days at which point the reactor shut down due to excessive pressure drop. The catalyst had swelled to almost twice its original volume and plugged the reactor. At the end of the run, the conversion and selectivity were 99.8% and 98.0%, respectively. The resin swelling rate decreased to 2.7%/day.

Example 9 (Comparative Example)

For example 9, the catalyst used in Example 1 was converted to the citrate anion form by pumping a solution of citric acid (5 wt. %) through it. The citrate-exchanged resin was then loaded into the reactor described above and the ethylene oxide and water again reacted over the catalyst. No additive was present in the feed. In this example the maximum reaction temperature was allowed to reach 130° C.

The reaction was continued for 30 days at which point the reactor shut down due to excessive pressure drop. The catalyst had swelled to twice its original volume and plugged the reactor. At the end of the run, the conversion and selectivity were 99.5% and 97%, respectively. The resin swelling rate was 3.3%/day.

Example 10 (Comparative)

For Example 10, the procedure used in Example 1 to prepare the catalyst and to start the reaction was repeated. In this example, the maximum reaction temperature was allowed to reach 130° C. To reduce swelling 140 ppm of $CO_2$ was added to feed mixture. At the beginning of the run, the conversion and selectivity were greater than 99% and 98.6%, respectively.

The reaction was continued for 34 days at which point the reactor shut down due to excessive pressure drop. The catalyst had swelled to more than twice its original volume and plugged the reactor. At the end of the run, the conversion and selectivity were 97.0% and 98.1%, respectively. The resin swelling rate was 4.5%/day.

Example 11

For example 11, the procedure used in Example 2 to prepare the catalyst and to start the reaction was repeated. In this example the maximum reaction temperature was allowed to reach 130° C. To slow down the rate of swelling and preserve the catalyst reactivity, 25 ppm by weight of tricarballylic acid was added to the aqueous feed. Initially, the conversion was more than 99.8% and the selectivity was 95.8%.

The reaction was continued for 34 days at which point the reactor shut down due to excessive pressure drop. The catalyst had swelled to almost twice its original volume and plugged the reactor. At the end of the run, the conversion and selectivity were 96.6% and 93.2%, respectively. The resin swelling rate decreased to 5.0%/day. Even though an improvement in swelling was achieved, the selectivity of the reaction to mono-ethylene glycol was reduced.

Example 12

For example 12, the procedure used in Example 1 to prepare the catalyst and to start the reaction was repeated. In this example the maximum reaction temperature was allowed to reach 130° C. To slow down the rate of swelling and preserve the catalyst reactivity, 25 ppm by weight of ethylene diamine tetra acetic acid was added to the aqueous feed. Initially, the conversion was greater than 99.9% and the selectivity was in excess of 95.9%.

The reaction was continued for 20 days at which point the reactor shut down due to excessive pressure drop. The catalyst had swelled to almost twice its original volume and plugged the reactor. At the end of the run, the conversion and selectivity were more than 99.9% and greater than 96.3%, respectively. The resin swelling rate decreased to 4.2%/day. Even though an improvement in swelling was achieved, the selectivity of the reaction to mono-ethylene glycol was reduced.

The results from the various examples and comparative examples above are summarized in Table 1:

TABLE 1

Comparative Swelling Rates

| Example | Ion Exchange Resin | Anion Form | Feed Additive | Maximum T° C. | % Swell/day |
|---|---|---|---|---|---|
| 1 (comp) | Mitsubishi XSA 1000 | Bicarbonate | None | 130 | 6.7 |
| 2 (comp) | Marathon A | Bicarbonate | None | 118 | 2.1 |
| 3 (comp) | Marathon A | Bicarbonate | None | 125 | 5.1 |
| 4 (comp) | Marathon A | Bicarbonate | None | 130 | 10.1 |
| 5 (comp) | Marathon A | Bicarbonate | None | 133 | 17.4 |
| 6 | Marathon A | Bicarbonate | 25 ppm CA | 130 | 3.9 |
| 7 | Marathon A | Bicarbonate | 50 ppm CA | 130 | 1.3 |
| 8 | Mitsubishi XSA 1000 | Bicarbonate | 25 ppm CA | 130 | 2.7 |
| 9 (comp) | Mitsubishi XSA 1000 | Citrate | None | 130 | 3.3 |
| 10 (comp) | Mitsubishi XSA 1000 | Bicarbonate | 140 ppm $CO_2$ | 130 | 4.5 |
| 11 | Marathon A | Bicarbonate | 25 ppm TCA | 130 | 5.0 |
| 12 | Mitsubishi XSA 1000 | Bicarbonate | 25 ppm EDTA | 130 | 4.2 |

CA-Citric Acid, TCA-tricarballylic acid, EDTA-ethylene diamine tetra acetic acid.

The examples show advantages to adding citric acid to the reaction feed. For a Mitsubishi resin converted to the bicarbonate form, the swelling rate is reduced to 2.7% per day from 6.7% per day when 25 ppm of citric acid is added to the feed. For a Marathon A resin converted to the bicarbonate form, the resin swelling rate is only 1.3% when 50 ppm of citric acid is added to the feed and the reaction temperature is 130° C. This compares favorably to examples run at 125° C., 130° C. and 133° C., where the swelling rates were 5.1%, 10.1% and 17.4%, respectively.

To further demonstrate the benefits provided by the additives, the swelling rates for the Mitsubishi catalyst converted to the bicarbonate form were compared to the same catalyst converted to citrate form. The feed mixture fed to the reactor containing catalyst in the bicarbonate form had 25 ppm of citric acid, whereas the feed to citrate exchanged catalyst had no additive. In this comparison, feeding a citrate anion additive resulted in a reduction of swelling from 2.7% per day versus 3.2% per day when the resin was pre-exchanged to the citrate form.

What is claimed is:

1. A method for making an alkylene glycol comprising:

feeding an alkylene oxide and water to a reaction zone, the reaction zone comprising an anion exchange resin catalyst;

feeding anion in acid form, selected from the group consisting of polycarboxylic acids containing at least two carboxylic acid groups to the reaction zone; and maintaining a temperature of at least 80° C. in the reaction zone.

2. The method of claim 1 wherein the catalyst comprises an anion exchange resin in the bicarbonate form, the citrate form or the oxalate form.

3. The method of claim 1 wherein the alkylene glycol is ethylene glycol, propylene glycol or butylene glycol, and the alkylene oxide is ethylene oxide, propylene oxide or butylene oxide.

4. The method of claim 1 wherein the anion in acid form is selected from the group consisting of citric acid and oxalic acid.

5. The method of claim 4, wherein the anion in acid form is citric acid.

6. The method of claim 1, wherein the anion in acid form is fed to the reaction zone in a concentration of between 10 and 150 ppm.

7. The method of claim 6, wherein the anion in acid form is fed to the reaction zone in a concentration of between 25 and 100 ppm.

8. The method of claim 1 wherein the reaction zone comprises at least one adiabatic reactor.

9. The method of claim 1, wherein the reaction temperature is between 100° C. and 140° C.

10. The method of claim 9, wherein the reaction temperature is between about 120° C. and 135° C.

11. The method of claim 2 wherein the anion exchange resin is oxalate form.

12. The method of claim 4 wherein the anion in acid form is oxalic acid.

13. The process of claim 1 wherein the anion in acid form is oxalic acid, and the anion exchange resin is in oxalate form.

* * * * *